US00PP08563P

United States Patent [19]

Drewlow

[11] Patent Number: Plant 8,563

[45] Date of Patent: Jan. 25, 1994

[54] POINSETTIA PLANT NAMED DONNER

[75] Inventor: Lyndon W. Drewlow, Ashtabula, Ohio

[73] Assignee: Mikkelsens, Inc., Ashtabula, Ohio

[21] Appl. No.: 22,346

[22] Filed: Feb. 24, 1993

[51] Int. Cl.[5] ..... A01H 5/00
[52] U.S. Cl. ..... Plt./86.4
[58] Field of Search ..... Plt. 86.4

*Primary Examiner*—James R. Feyrer
*Attorney, Agent, or Firm*—Foley & Lardner

[57] ABSTRACT

A new and distinct cultivar of poinsettia plant named Donner, produced by grafting a seedling from the cross described to a plant of Super Rochford for the purpose of transferring the excellent branching characteristics of Super Rochford. Donner is characterized by its red, relatively large bracts, strong, vigorous growth habit, very early flowering, excellent branching, excellent foliage retention, resistance to heat delay of flower bud initiation when night temperatures are above 23° C., medium dark green leaves, and small cyathia cluster.

2 Drawing Sheets

The present invention relates to a new and distinctive cultivar of poinsettia plant, botanically known as *Euphorbia pulcherrima*, and referred to by the cultivar name Donner.

Donner was developed by me through controlled breeding by crossing Mikkelsen Seedling No. 87-240-1 (seed parent) with Mikkelsen Seedling No. 86-131-1 (pollen parent). One of the seedlings from the cross was characterized by red bracts and poor branching. This seedling was identified by No. 88-457-1. This seedling was then grafted to the excellent branching type cultivar Super Rochford (not patented) in an attempt to transfer the branching habit of Super Rochford to the red seedling. The graft was successful, resulting in the seedling having the branching habit of Super Rochford and retaining all other desirable characteristics of the new seedling.

Asexual reproduction by stem cuttings in a greenhouse in Ashtabula, Ohio has shown that the unique features of this new poinsettia are stabilized and are reproduced true to type in successive propagations.

The following characteristics distinguish Donner from both its parent cultivars and other cultivated poinsettia of this type known and used in the fluoriculture industry.

1. When 5 or more nodes are left after a pinch (apical tip removal) Donner will develop full length shoots from each node like Super Rochford, Yeletide (U.S. Plt. Pat. No. 7,316), and Feliz Navidad (plant patent pending), while the original seedling 88-4571 will develop a full length shoot only from the upper 3 nodes, with the balance of shoots being greatly repressed.

2. Donner at 26 to 28 cm is shorter than the 88-457-1 seedling at 30 to 32 cm when similar size plants are left after pinching, because there is little or no apical dominance in the branched types. Thus, lower breaks may grow longer than top breaks on a plant instead of the top 3 shoots becoming dominant. Super Rochford is taller at 34 to 36 cm. Yuletide and Feliz Navidad are similar at 26 to 28 cm.

3. Donner has slightly lighter green leaves than the original seedling 88-457-1, but the leaf color of Donner is similar to Super rochford and Yuletide , with all of these cultivars being classified 147A in color (R.H.S. Colour Chart).

4. is more tolerant than 88-457-1 to low light levels and high temperatures of the average home as leaves do not yellow and drop like 88-457-1 under these conditions. When kept moist, Donner has excellent foliage retention, similar to the comparison cultivars.

5. Bract coloration of Donner is 46B to 46C (R.H.S.), which is a lighter red than the 46B of seedling 88-457-1, with the bracts of Feliz Navidad being a still lighter red 45B to 45C.

6. Donner has a cyathia cluster (flowers in center of bract) that is slightly smaller in number and diameter (2–3 cm) than the original seedling 88-457-1; much smaller than Yuletide, Super Rochford, and similar to Feliz Navidad.

7. Donner is resistant to heat delay of flower bud initiation when night temperatures are above 23° C., similar to 88-457-1 and Feliz Navidad, with Yuletide being slightly susceptible and Super Rochford very susceptible to heat delay. This is of commercial importance, especially in the southern U.S.A. and warmer than normal autumns in the north.

8. Bract size of Donner is similar to Feliz Navidad at 30 to 32 cm, which is larger than Yuletide (26 to 28 cm) and Super Rochford at 20 to 25 cm. Bracts are not as reflexed as Feliz Navidad but more reflexed than Yuletide and Super Rochford. Cyathia will not split apart like Super Rochford but remain in a tight cluster like Yuletide and Feliz Navidad.

9. All other characteristics of Donner are similar to the original seedling, 88-457-1, such as early flowering under natural short days, similar shaped leaves and bracts, retention of cyathia under stress conditions and non-splitting cyathia.

The accompanying colored photographs illustrate the overall appearance of Donner, and show the colors as true as is reasonably possible to obtain in colored reproductions of this type. The photograph on sheet 1 is a front perspective view showing the foliage and bracts of a typical plant of Donner. The photograph on sheet 2 is a top perspective view of the plant, showing the bracts more clearly. The photographs were taken on Nov. 26, 1991 in a rigid fiberglass greenhouse on an overcast day in Ashtabula, Ohio.

The following detailed description of my new cultivar, based on plants produced in greenhouses in Ashtabula, Ohio during the Fall season of the year. Plants were grown in 15 cm pots and measurements were taken seventeen (17) weeks after rooted cuttings were planted. Height measurements were taken from the soil line of the container. The plants were grown at 64°-68° F. night temperatures, under 3500-4000 foot candles of light, and with 250 ppm Nitrogen, 75 ppm Potassium, and 250 ppm Phosphorous nutritional levels, with trace elements added. Habit of growth, foliage coloration, leaf variegation, size of leaves and flower size will be influenced by nutritional and environmental conditions, without, however, any variation in genotype.

Color references are made to The Royal Horticultural Society Colour Chart except where general terms of ordinary dictionary significance are used.

Parentage: Controlled cross between female Mikkelsen Seedling No. 87-240-1 and male Mikkelsen Seedling No. 86-131-1; resulting seedling (88-457-1) then grafted to a plant of Super Rochford.

Propagation:

A. *Type cutting.*—Stem 5 to 6 cm long.

B. *Time to root.*—14 days at 21° C. Summer; 18 days at 21° C. Winter.

C. *Rooting habit.*—Abundant, thick, fibrous roots.

Plant description:

A. *Form.*—Upright; when apical meristem is removed (pinching) leaving 5 or more nodes above soil line to pot, generally all lateral shoots will emerge and develop.

B. *Habit of growth.*—Strong, thick stems with excellent branch angles that hold bracts up for good display of color. Bottom stems break first and elongate faster than upper stems, resulting in the upright growth habit with bract display on upper ⅔ of plant. Growth is vigorous and Donner can easily be grown with use of proper scheduling system without chemical growth regulators.

C. *Foliage.*—Leaves are alternate and borne on 5.0 to 6.0 cm long petioles which have a reddish purple cast. The last 2-3 leaves before true bract leaves also turn the same red color as bracts. 1. Size: Mature leaves are 12 to 14 cm long and 7 to 9 cm wide at broadest point near basal area of leaf. 2. Shape: More lanceolate than ovate with acuminate apex and rounded base. 3. Texture: Upper glabrous; lower glabrous and rugose because of protruding veins. 4. Margin: Entire. 5. Color: Young foliage, top side, closest to but slightly darker than 144A. under side, 146B. Mature foliage, top side, 147A. under side, 147B.

Flowering description:

A. *Flowering habits.*—Earliest flowering cultivar that inventor has developed; Donner appears to have a longer critical daylength for flower initiation. Under controlled daylength, development time is approximately 8 weeks and appears even earlier because last 2 or 3 true leaves turn red before bract fully develops. The early flower initiation is of commercial significance.

B. *Natural flowering season.*—November 10 to 15 under Ohio conditions. Flowering time under 11 hours of daylength at 20° C. is 8 weeks. Donner does not heat delay (failure to set flower bud under night temperature above 23° C.).

C. *Cyathia description.*—Few in number in tight cluster at center of bract; are stress tolerant, remaining in the involucre for a considerable time under low fertility, low light, high temperature conditions even after pollen shed. Severe drying may cause them to drop.

D. *Cyathia borne.*—Stay closely clustered without growing apart (splitting). Usually 2 to 3 cm in diameter. Flowering can be initiated any time of the year by controlling the daylength to approximately 11 hours total. Cyathia will continue to initiate until daylength is greater than approximately 13 hours.

E. *Quantity of Cyathia.*—Quantity is highly dependent on cultural practices and can vary from minimum of 2 to 3 to more than 10.

F. *Bracts.*—1. Shape: First true bracts are more lanceolate, with later formed bracts more oblong. First bracts 11 to 12 cm long and 6 to 7 cm wide with a 2 to 3 cm petioles; later bracts are 7 to 8 cm long and 3.5 to 4.0 cm wide with 10 cm petioles. 2. Color at maturity: Upper side 46B to 46c, under side 45C; young bract is similar in color except greenish when very immature. 3. Number of bracts: 10 to 15 normal number but could be fewer or more depending on growing conditions. Bract diameter varies with growing conditions; for example, if plants are pinched and growth regulators are used.

G. *Reproductive organs.*—1. Stamens: numerous. a. Anther shape: oblong, color reddish. b. Filament color: reddish. c. Pollen color: yellow. 2. Pistels: a. Stigma shape: forked, color reddish. b. Style color: reddish. c. Ovaries: Celled, 3 in number, 3 mm when stigma is receptive, green. 3. Nectar cups: Generally 2 nectar cups on each cyathia, with none or 1 occurring rarely; nectar readily available on maturing cyathia.

Disease resistance: Bracts are very resistant to botrytis damage even on very old bracts (30 days or longer from full expansion). Small cyathia area helps prevent botrytis after nectar cups start exuding honey-like substance.

OTHER IMPORTANT CHARACTERISTICS

A. Upright growth habit with strong stems and excellent branch angles to hold up large bracts make Donner excellent for faster and easier sleeving for shipping without branch breakage.

B. Earliest flowering poinsettia cultivar developed to date under natural short days, thereby eliminating the need for black cloth for early November sales.

C. The leaves and bracts of Donner are more lanceolate than the more ovate leaves and bracts of Yuletide and Feliz Navidad, thereby providing variation in bract and leaf form.

D. With proper scheduling Donner can be grown without growth regulators, thereby eliminating both a crop expense and a potential environmental hazard.

I claim:

1. A new and distinct cultivar of poinsettia plant named Donner, as illustrated and described.

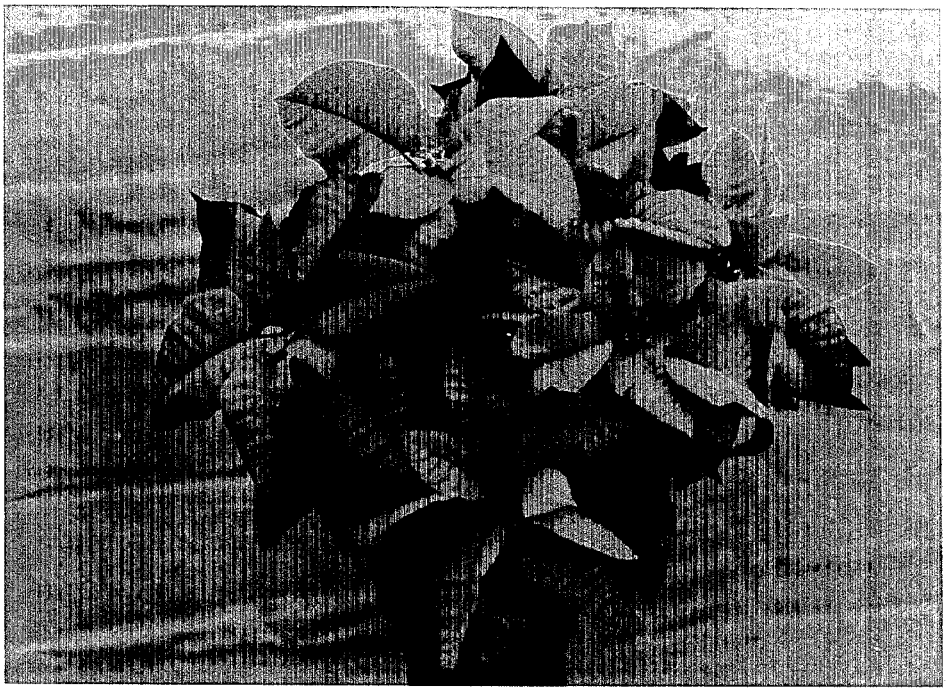

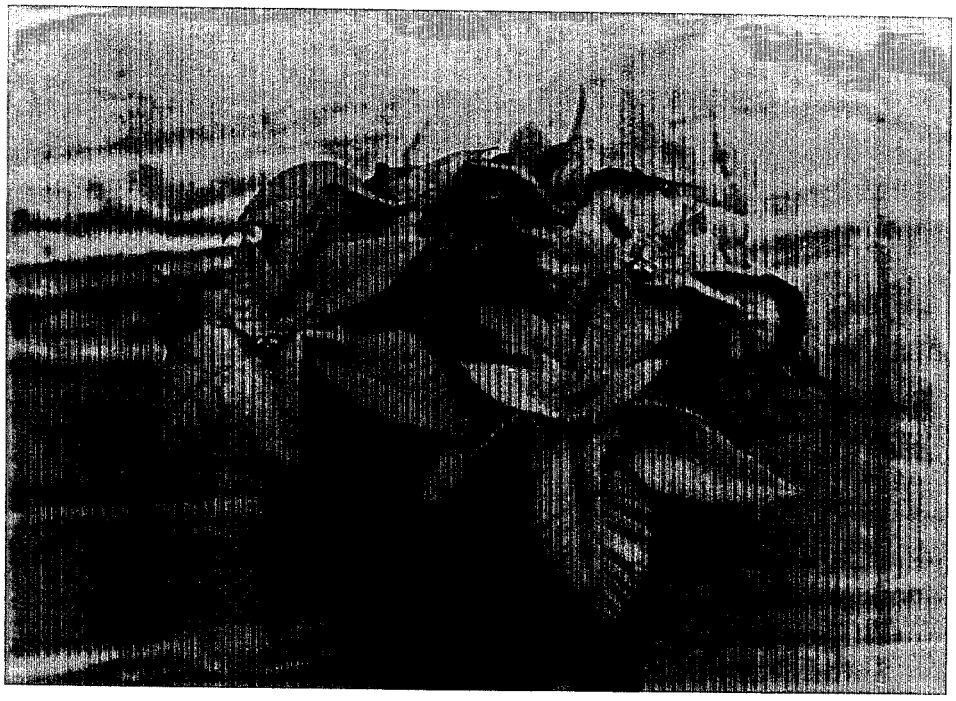

* * * * *